US009630899B1

(12) United States Patent
Huang et al.

(10) Patent No.: US 9,630,899 B1
(45) Date of Patent: Apr. 25, 2017

(54) PROCESS FOR PRODUCING HYDROQUINONE AND DERIVATES

(71) Applicant: Chang Chun Plastics Co. Ltd., Taipei (TW)

(72) Inventors: Chien Fu Huang, Taipei (TW); Yi Hung Chou, Taipei (TW)

(73) Assignee: Chang Chun Plastics Co. Ltd., Taipei (TW)

( * ) Notice: Subject to any disclaimer, the term of this patent is extended or adjusted under 35 U.S.C. 154(b) by 0 days.

(21) Appl. No.: 14/922,358

(22) Filed: Oct. 26, 2015

(51) Int. Cl.
*C07C 46/06* (2006.01)
*C07C 45/28* (2006.01)
*C07C 37/60* (2006.01)

(52) U.S. Cl.
CPC .............. *C07C 46/06* (2013.01); *C07C 37/60* (2013.01); *C07C 45/28* (2013.01)

(58) Field of Classification Search
None
See application file for complete search history.

(56) References Cited

U.S. PATENT DOCUMENTS

| | | | | |
|---|---|---|---|---|
| 3,662,006 | A | * | 5/1972 | Massie et al. .......... C07C 37/60 568/629 |
| 4,578,521 | A | * | 3/1986 | Chang .................... C07C 37/60 568/771 |
| 5,493,061 | A | | 2/1996 | Ratnasamy et al. |
| 6,180,836 | B1 | * | 1/2001 | Cheng .................... C07C 37/60 568/803 |
| 6,262,315 | B1 | | 7/2001 | Inaba et al. |
| 6,872,857 | B1 | | 3/2005 | Dewkar et al. |
| 6,900,358 | B2 | | 5/2005 | Hamilton, Jr. |
| 7,148,386 | B2 | | 12/2006 | Thampi et al. |
| 7,285,688 | B2 | | 10/2007 | Kanougi et al. |
| 9,061,982 | B2 | | 6/2015 | Ernst et al. |
| 2004/0063568 | A1 | * | 4/2004 | Kuhnle .............. B01D 53/8628 502/60 |
| 2008/0227984 | A1 | | 9/2008 | Greenhill-Hooper et al. |
| 2014/0329959 | A1 | | 11/2014 | Barnes et al. |

FOREIGN PATENT DOCUMENTS

| | | |
|---|---|---|
| CN | 101239890 A | 8/2008 |
| CN | 102351656 B | 9/2013 |
| CN | 102336643 B | 6/2014 |

(Continued)

OTHER PUBLICATIONS

Kunai et al. ("Pd/SiO2 catalyst for oxidation of Benzene to Phenol", Catalysis Letters, vol. 4, Issue 2, Mar. 1990).*

(Continued)

*Primary Examiner* — Rosalynd Keys
(74) *Attorney, Agent, or Firm* — Polsinelli PC

(57) ABSTRACT

The present disclosure relates to an improved, environmentally friendly, process for producing compounds such as hydroquinone (benzene-1,4-diol) and its derivatives. The process can be carried out at ambient temperature and pressure using a recyclable copper catalyst and recyclable intermediate materials. The process generally entails reacting an aromatic compound such as benzene with hydrogen peroxide in the present of a pure elemental copper catalyst or a copper (I) salt catalyst to form oxidation product such as benzoquinone, and reducing the compound to hydroquinone or a hydroquinone derivative.

20 Claims, 4 Drawing Sheets

(56) References Cited

FOREIGN PATENT DOCUMENTS

| CN | 102675052 B | 6/2014 |
|---|---|---|
| EP | 0093540 A2 | 11/1983 |
| EP | 0962439 A1 | 12/1999 |
| EP | 2597080 A1 | 5/2013 |
| WO | WO-2005063664 A1 | 7/2005 |
| WO | WO-2006038893 A1 | 4/2006 |
| WO | WO-2006015036 A3 | 8/2006 |

OTHER PUBLICATIONS

Peter P.-Y. Chen et al., "Development of the tricopper cluster as a catalyst for the efficient conversion of methane into MeOH," Chemcatchem; 2014, 6, 429-437.

Sunney I. Chan et al., "Efficient catalytic oxidation of hydrocarbons mediated by tricopper clusters under mild conditions," Journal of Catalysis 293 (2012) 186-194.

Sunney I. Chan et al., "Efficient Oxidation of Methane to Methanol by Dioxygen Mediated by Tricopper Clusters," Angew. Chem. Int. Ed. 2013, 52, 3731-3735.

Penumaka Nagababu et al., Efficient Room-Temperature Oxidation of Hydrocarbons Mediated by Tricopper Cluster Complexes with Different Ligands, Adv. Synth. Catal. 2012, 354, 3275-3282.

Peter P.-Y. Chen et al., "Facile O-atom insertion into COC and COH bonds by a trinuclear copper complex designed to harness a singlet oxene," PNAS, Sep. 11, 2007, vol. 104,No. 37, 14570-14575.

Suman Maji et al., "Dioxygen Activation of a Trinuclear CuICuICuI Cluster Capable of Mediating Facile Oxidation of Organic Substrates: Competition between O-Atom Transfer and Abortive Intercomplex Reduction," Chem. Eur. J. 2012, 18, 3955-3968.

Peter R. Makgwane et al., "Hydroxylation of benzene to phenol over magnetic recyclable nanostructured CuFe mixed-oxide catalyst," Journal of Molecular Catalysis A: Chemical 398 (2015) 149-157.

Salam J.J. Titinchi, et al., "Tri- and tetradentate copper complexes: a comparative study on homogeneous and heterogeneous catalysis over oxidation reactions," Catal. Sci. Technol., 2015,5, 325-338.

Xiu Yuan et al., "Copper-Catalyzed Hydroquinone Oxidation and Associated Redox Cycling of Copper under Conditions Typical of Natural Saline Waters," Environ. Sci. Technol., 2013, 47 (15), Abstract.

Tao Jiang et al., "Catalytic hydroxylation of benzene to phenol with hydrogen peroxide using catalysts based on molecular sieves," New J. Chem., 2013,37, Abstract.

Azarifar, Davood et al., "Tetrakis(acetonitrile)copper(I) Hexafluorophosphate as an Efficient Catalyst for the Synthesis of Triazolo[1,2-a]indazole-1,3,8-trione and 2Hindazolo[2,1-b]phthalazine-trione Derivatives," Letters in Organic Chemistry, vol. 9, No. 2, Feb. 2012, Abstract.

Jun-Qin Qiao et al., "Determination of catalytic oxidation products of phenol by RP-HPLC," Research on Chemical Intermediates, Feb. 2012, vol. 38, Issue 2, Abstract.

* cited by examiner

PROCESS FOR PRODUCING HYDROQUINONE AND DERIVATES

FIELD OF THE DISCLOSURE

The present disclosure relates to an improved, environmentally friendly, process for producing compounds such as hydroquinone (benzene-1,4-diol) and its derivatives. The process can be carried out at ambient temperature and pressure using a recyclable copper catalyst and recyclable intermediate materials.

BACKGROUND

Hydroquinone (or 1,4-dihydroxybenzene) has many uses. Many of the uses are associated with hydroquinone's action as a reducing agent that is soluble in water. For example, hydroquinone is used as a developing agent in black-and-white photography, lithography, and x-ray films. It is also used as an intermediate to produce antioxidants for rubber and food. Furthermore, it is added to a number of industrial monomers to inhibit polymerization during shipping, storage, and processing. As a polymerization inhibitor, hydroquinone prevents polymerization of acrylic acid, methyl methacrylate, cyanoacrylate, and other monomers that are susceptible to radical-initiated polymerization.

Hydroquinone can undergo mild oxidation to convert to the compound parabenzoquinone, $C_6H_4O_2$, often called p-quinone or simply quinone. Reduction of quinone reverses this reaction back to hydroquinone. Some biochemical compounds in nature have this sort of hydroquinone or quinone section in their structures, such as Coenzyme Q, and can undergo similar redox interconversions.

In human medicine, hydroquinone is sometimes used topically for skin whitening and/or to reduce the color of skin. Hydroquinone is sometimes combined with alpha hydroxy acids that exfoliate the skin to quicken the lightening process. There are several disadvantages of existing hydroquinone manufacturing process, such as low selectivity; highly polluted waste stream; high reaction temperature and energy cost.

SUMMARY OF THE DISCLOSURE

The instant disclosure relates to a process for producing hydroquinone and hydroquinone derivatives. The process is particularly advantageous because it does not produce catechol, which is a common by-product in the manufacture of hydroquinone. Furthermore, the process uses hydrogen peroxide as the oxidant resulting in the formation of water and oxygen, which are both non-polluting compounds. The copper catalyst can be recycled and re-used multiple times. Therefore, the process is environmentally friendly. Finally, the process can be carried out at room temperature and pressure, and therefore does not require huge amounts of energy.

FIG. 1 illustrates three common mechanism that can be used to manufacture hydroquinone: (1) analine oxidation; (2) diisopropylbenzene (DIPB) oxidative cleavage; and (3) phenol hydroxylation. See, e.g., FIG. 1. The advantages that the instant process (inventive process) provides over these other three common mechanisms are summarized in the following table.

| Process | Features |
|---|---|
| Inventive Process | |
| Direct Oxidation of Benzene According to the Instant Disclosure | The instant process be carried out continuously and provides for yields of at least 60% under mild reaction conditions, i.e., at room temperature and ambient pressure. The byproduct phenol (B.P. 181.7° C.) is easy to separate and recycled. Also the catalyst can continually be regenerated and recycled. Thus, it is "clean" and "environmentally friendly." |
| Comparative Processes | |
| Aniline Oxidation | Although this process can provide high yields, it produces substantial amounts of waste (Fe/Mn metal ions). Also this process cannot be carried out continuously-it must be processed batch-wise. These factors contribute to high cost. |
| DIPB Oxidative Cleavage | Although this process is less costly than the analine oxidation process (about 30% less costly than the aniline process), it produces impurities and low cost byproducts such as acetone. |
| Phenol Hydroxylation | Although this process uses hydrogen peroxide as the oxidant, which does not cause pollution, it has very low yields; less than 50%. It also produces Catechol (B.P. 245.5° C.) as a by-product, which is difficult and costly to separate. |

The instant process for producing hydroquinione and hydroquinone derivatives (compounds of Formula (III)) generally comprises:

(A) reacting a compound of Formula (I) with hydrogen peroxide in the presence of elemental copper catalyst or a copper (I) salt catalyst to form the oxidation product of Formula (II):

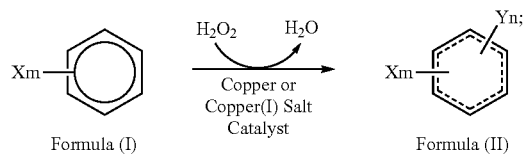

wherein each X is independently a halogen, a $C_1$-$C_8$ alkyl, a $C_1$-$C_8$ alkenyl, a $C_1$-$C_8$ alkoxy, a $C_3$-$C_8$ cycloalkyl, or a $C_6$-$C_{20}$ aryl group; each Y is independently a carbonyl or a hydroxyl; n is an integer from 1 to 3; and m is an integer from 0 to 4; and (B) converting the oxidation product of Formula (II) to a compound of Formula (III) by reduction:

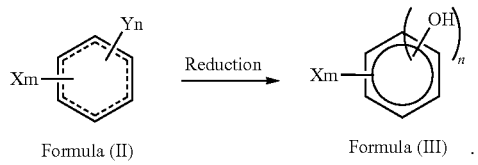

The catalyst for reacting a compound of Formula (I) with hydrogen peroxide can be an elemental copper catalyst or a copper (I) salt catalyst, for example a tetrakis(acetonitrile) copper (I) salt having the following formula: $Cu(CH_3CN_4)$-A, wherein A is an anion. For example, the anion may be $ClO_4^-$, $NO_3^-$, $BF_4^-$, $PF_6^-$, and $CF_3SO_3^-$.

The reaction of the compound of Formula (I) with hydrogen peroxide is typically carried out in a solvent. The solvent may be, for example, a nitrile, a $C_3$-$C_7$ ketone, a $C_5$-$C_{10}$ ether, a $C_2$-$C_7$ ester, or a $C_5$-$C_{10}$ hydrocarbon. Examples of a nitrile include, but are not limited to, acetonitrile, propionitrile, butanenitrile, and benzonitrile. In some cases, acetonitrile is used as the solvent in the reaction of the compound of Formula (I) with hydrogen peroxide.

The process can be specific for producing hydroquinone by using benzene as the compound of Formula (I) and reacting it with hydrogen peroxide in the presence of elemental copper catalyst or a copper (I) salt catalyst to form benzoquinone and phenol, and converting the benzoquinone to hydroquinone by reduction.

BRIEF DESCRIPTION OF THE DRAWINGS

Implementations of the present technology will now be described, by way of example only, with reference to the attached figures, wherein.

Figure 1:
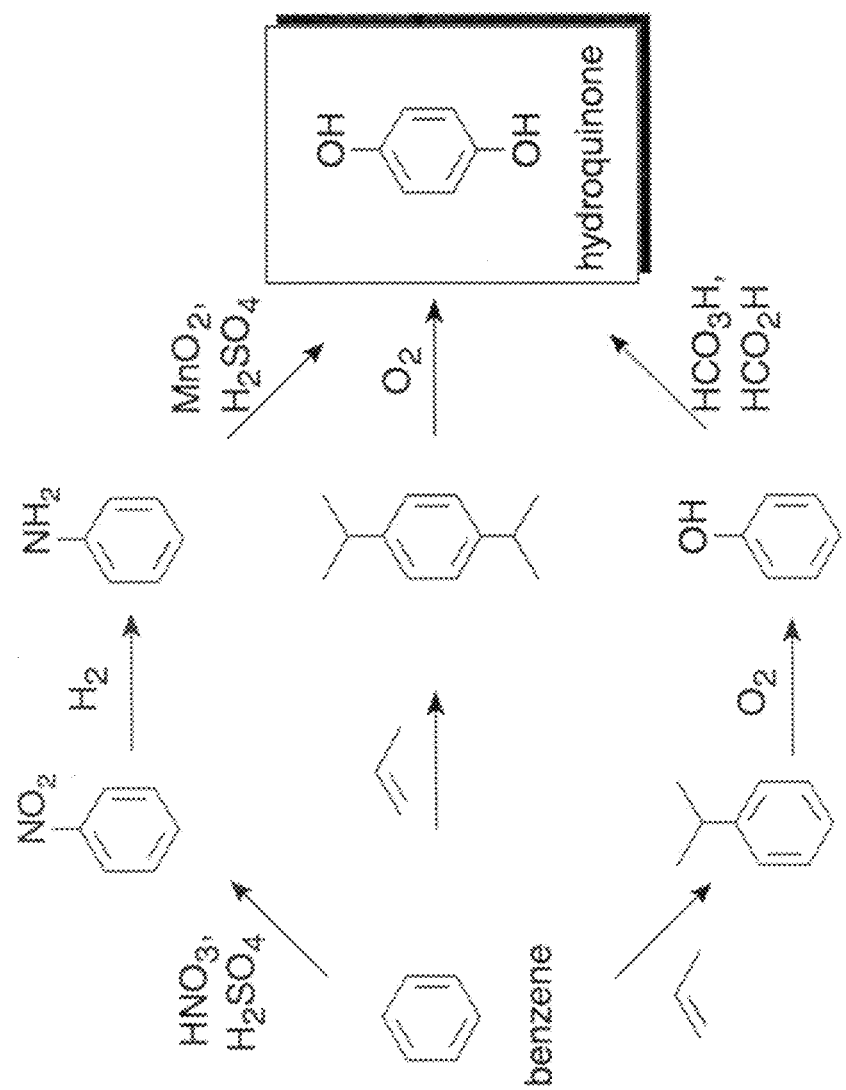
FIG. 1 is a diagram illustrating various methods that are used to produce hydroquinone.

It should be understood that the various aspects are not limited to the arrangements and instrumentality shown in the drawings.

DETAILED DESCRIPTION OF THE DISCLOSURE

The process for producing hydroquinione and hydroquinone derivatives (compounds of Formula (III)) generally comprises:

(A) reacting a compound of Formula (I) with hydrogen peroxide in the presence of an elemental copper catalyst or a copper (I) salt catalyst to form the oxidation product of Formula (II):

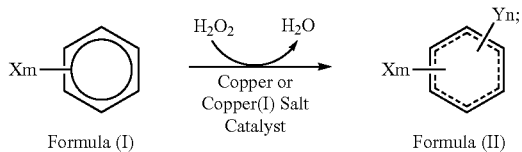

wherein each X is independently a halogen, a $C_1$-$C_8$ alkyl, a $C_1$-$C_8$ alkenyl, a $C_1$-$C_8$ alkoxy, a $C_3$-$C_8$ cycloalkyl, or a $C_6$-$C_{20}$ aryl group; each Y is independently a carbonyl or a hydroxyl; n is an integer from 1 to 3; and m is an integer from 0 to 4; and (B) converting the oxidation product of Formula (II) to a compound of Formula (III) by reduction:

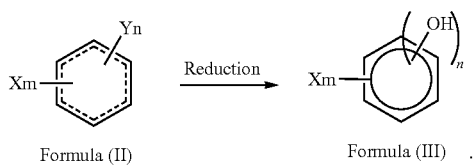

The catalyst for reacting a compound of Formula (I) with hydrogen peroxide can be an elemental copper catalyst or a copper (I) salt catalyst, for example a tetrakis(acetonitrile) copper (I) salt having the following formula: $Cu(CH_3CN_4)$-A, wherein A is an anion. The anion may be, for example, $ClO_4^-$, $NO_3^-$, $BF_4^-$, $PF_6^-$, and $CF_3SO_3^-$. Typically, Formula (II) results in a mixture, wherein Y is hydroxyl on some compounds and carbonyl on other compounds. Therefore, a mixture of compounds of Formula (II) will often exist.

The reaction of the compound of Formula (I) with hydrogen peroxide is typically carried out in a solvent. The solvent may be, for example, a nitrile, a $C_3$-$C_7$ ketone, a $C_6$-$C_{10}$ ether, a $C_2$-$C_7$ ester, or a $C_6$-$C_{10}$ hydrocarbon. Examples of a nitrile include, but are not limited to, acetonitrile, propionitrile, butanenitrile, and benzonitrile. In some cases, acetonitrile is used.

The process can be carried out at room temperature and pressure. Room temperature is typically about 20 to about 30° C. (about 68 to about 86° F. and room pressure is typically about 1 atm. In some cases, the temperature can be from about 10° C. to about 80° C.; from about 15° C. to about 60° C., from about 15° C. to about 50° C., from about 15° C. to about 40° C., from about 15° C. to about 30° C., or from about 15° C. to 23° C., 24° C., or 25° C. Also, the temperature may be from about 15° C., 16° C., 17° C., 18° C., 19° C., or 20° C. to about 23° C., 24° C., 25° C., 26° C., 27° C., 28° C., 29° C., or 30° C.

The process allows for a selectivity of the compound of Formula (III) to be greater than about 60%. Nonetheless, the selectivity of the compound of Formula (III) may be greater than about 50%, 55%, 60%, 65%, 70%, 75%, 80%, 85%, 90%, or 95%. The process is particularly useful because the high selectivity (the high yields) are attained without the formation of catechol. Catechol is a by-product associated with the phenol hydroxylation method of synthesizing hydroquinone.

In some cases, the selectivity ratio for the desired product is at least about 2. The "selectivity ratio" is the ratio of the desired product formed (in moles) to the undesired product formed (in moles), i.e., moles of hydroquinone produces to the moles of phenol produced. The selectivity ratio, however, is typically higher than at least 2. For example, the selectivity ratio can be at least about 3, about 4, about 5, about 6, about 7, about 8, about 9, about 10, about 11, or higher. Often, the selectivity ratio is in the range of from about 3 to about 12, about 5 to about 11, or about 8 to about 11.

The process can be specific for producing hydroquinine by using benzene as the compound of Formula (I) and reacting it with hydrogen peroxide in the presence of elemental copper catalyst or a copper (I) salt catalyst to form benzoquinone and phenol, and converting the benzoquinone to hydroquinone by reduction. For instance, the process for producing hydroquinone may comprise:

(a) reacting benzene with hydrogen peroxide in the presence of elemental copper catalyst or a copper (I) salt catalyst dissolved in acetonitrile at a temperature of between 10° C. to 80° C.;

(b) separating a water phase from an oil phase generated in (a);

(c) using azeotropic distillation at a temperature of between 65° C. to 90° C. to remove the water and acetonitrile and optionally adding additional benzene and acetonitrile to the water phase;

(d) regenerating the used catalyst in (a);

(e) separating the mixture of benzoquinone and phenol from the unreacted benzene and acetonitrile;

(f) recycling the unreacted benzene and acetonitrile of (e) and using it as the additional benzene and acetonitrile added to the water phase in (c); and (g) converting the mixture of benzoquinone and phenol to hydroquinone by reduction.

Figure 2:
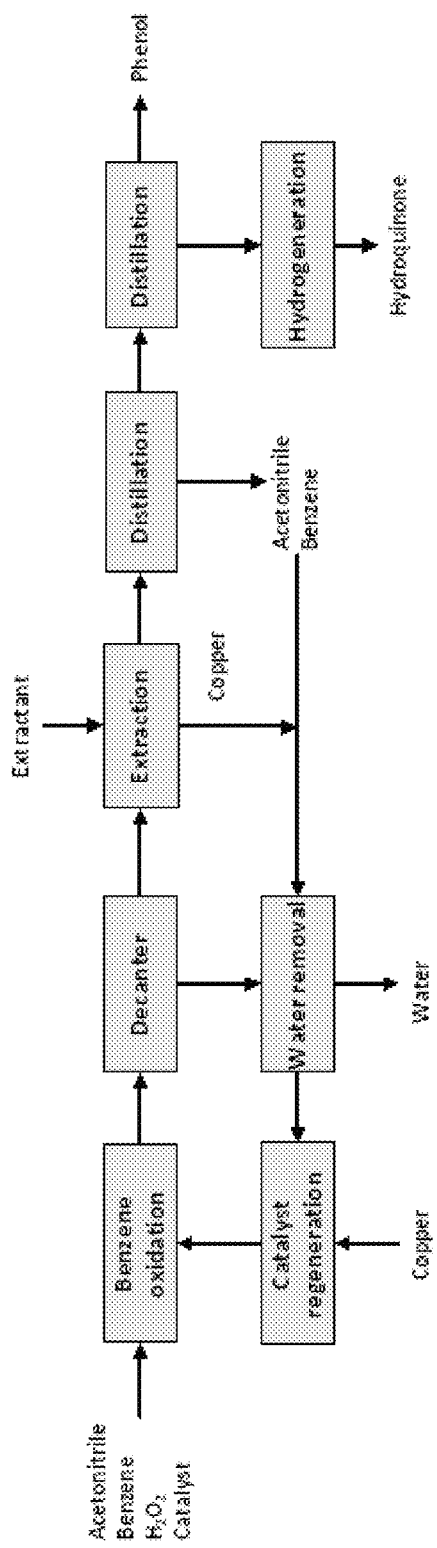
FIG. 2 is flow diagram illustrating an embodiment of the instant disclosure.

One embodiment of the instant disclosure is represented in FIG. 2, which is a flow diagram depicting various steps that can be incorporated into the process. Examples of various steps that may be included in the process include the following.

Oxidation of a Compound of Formula (I)

The oxidation of a compound of Formula (I) (e.g., benzene) can be carried out at room temperature and atmospheric pressure in a stirred reactor. A solvent, such as acetonitrile, can be used to dissolve the catalyst. Such a solvent functions as a co-solvent for benzene and hydrogen peroxide.

Water Removal

After carrying out the oxidation step described above, water can be removed by any method known in the art.

Catalyst Regeneration

The copper catalyst can be regenerated and re-used. The catalyst is regenerated by raising temperature above about 70° C., and using copper to revert the copper (II) to copper (I). Any un-reacted copper may be subsequently removed by filtration. Also, a packed bed (a hollow tube, pipe, or other vessel that is filled with a packing material, which is well-known to those in the art) can be used in this step.

Solvent/Compound of Formula (I) Recycle

A distillation tower can be used to separate product and un-reacted reactant (e.g., acetonitrile/benzene). The separated reactant can purge to the azeotropic distillation tower and be used as an entrainer.

Compound of Formula (II) Separation

By using extraction and distillation, the compound of formula (II) (e.g., benzoquinone) can be separated from the other materials and compounds produced (e.g., phenol).

Reduction of Compound of Formula (II)

The compound of formula (II) (e.g., benzoquinone) can be transformed to a compound of formula (III) (e.g., hydroquinone) by hydrogenation.

EXAMPLE 1

Synthesis of Hydroquinone with Tetrakis(acetonitrile)copper (I) Perchlorate Catalyst 3.30 g of copper perchlorate catalyst was dissolved in 350 g of acetonitrile (solvent). 197 g of benzene as added to the mixture. Hydrogen peroxide (10%) was also added (17.2 g of $H_2O_2$ and 155 g of $H_2O$). The reaction temperature was maintained at about 30° C. for 12 hours. The tetrakis(acetonitrile)copper (I) perchlorate catalyst was regenerated after the reaction and the process repeated 19 times. The results are graphically reported in FIG. 3.

Figure 3:
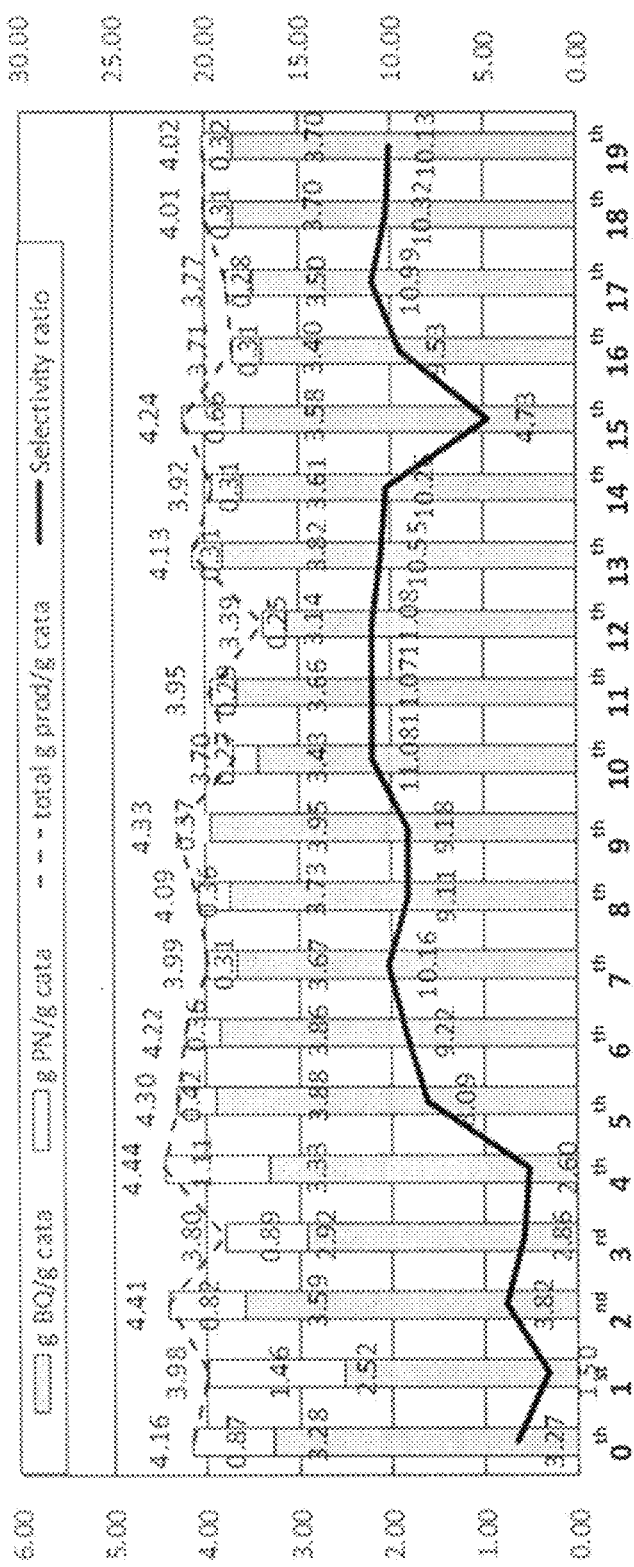
FIG. 3 provides experimental results using tetrakis(acetonitrile)copper (I) perchlorate as a catalyst.

FIG. 3 reports the grams of benzoquinone (BQ) produced per gram of catalyst; grams of phenyl (PN) produced per gram of catalyst; total grams of product produced per gram of catalyst; and the selectivity ratio. Please note that the "selectivity ratio" is the ratio of the desired product formed (in moles) to the undesired product formed (in moles), i.e., moles of hydroquinone produces to the moles of phenol produced. The table below presents the same data provided in FIG. 3 except that the selectivity for the hydroquinone is presented as a percentage of the total products produced (i.e., hydroquinone and phenol). As shown in the table below, in all cases the selectivity for hydroquinone was greater than 60% and in many cases higher than even 90%.

| Copper Perchlorate Catalyst | | |
| --- | --- | --- |
| Run | Selectivity Ration (moles of hydroquinone to moles of phenol) | Selectivity Percent (% of hydroquinone compared to total products produced) |
| 0 | 3.27 | 78.8 |
| 1 | 1.50 | 63.3 |
| 2 | 3.82 | 81.4 |
| 3 | 2.86 | 76.8 |
| 4 | 2.60 | 75.0 |
| 5 | 8.09 | 90.2 |
| 6 | 9.22 | 91.5 |
| 7 | 10.16 | 92.0 |
| 8 | 9.11 | 91.2 |
| 9 | 9.18 | 91.2 |
| 10 | 11.08 | 92.7 |
| 11 | 11.07 | 92.7 |
| 12 | 11.08 | 92.6 |
| 13 | 10.55 | 92.5 |
| 14 | 10.26 | 92.1 |
| 15 | 4.73 | 84.4 |
| 16 | 9.53 | 91.6 |
| 17 | 10.99 | 92.8 |
| 18 | 10.32 | 92.3 |
| 19 | 10.13 | 92.0 |

EXAMPLE 2

Synthesis of Hydroquinone with Pure Copper Catalyst 3 g of pure copper catalyst (copper powder) was dissolved in 350 g of acetonitrile (solvent). 197 g of benzene was added to the mixture. Hydrogen peroxide (10%) was also added (17.2 g of $H_2O_2$ and 154.8 g of $H_2O$). The reaction temperature was maintained at about 30° C. for 12 hours. The copper catalyst was regenerated (2 g of copper powder) after the initial reaction and the process repeated 8 times. The results are graphically reported in FIG. 4.

Figure 4:
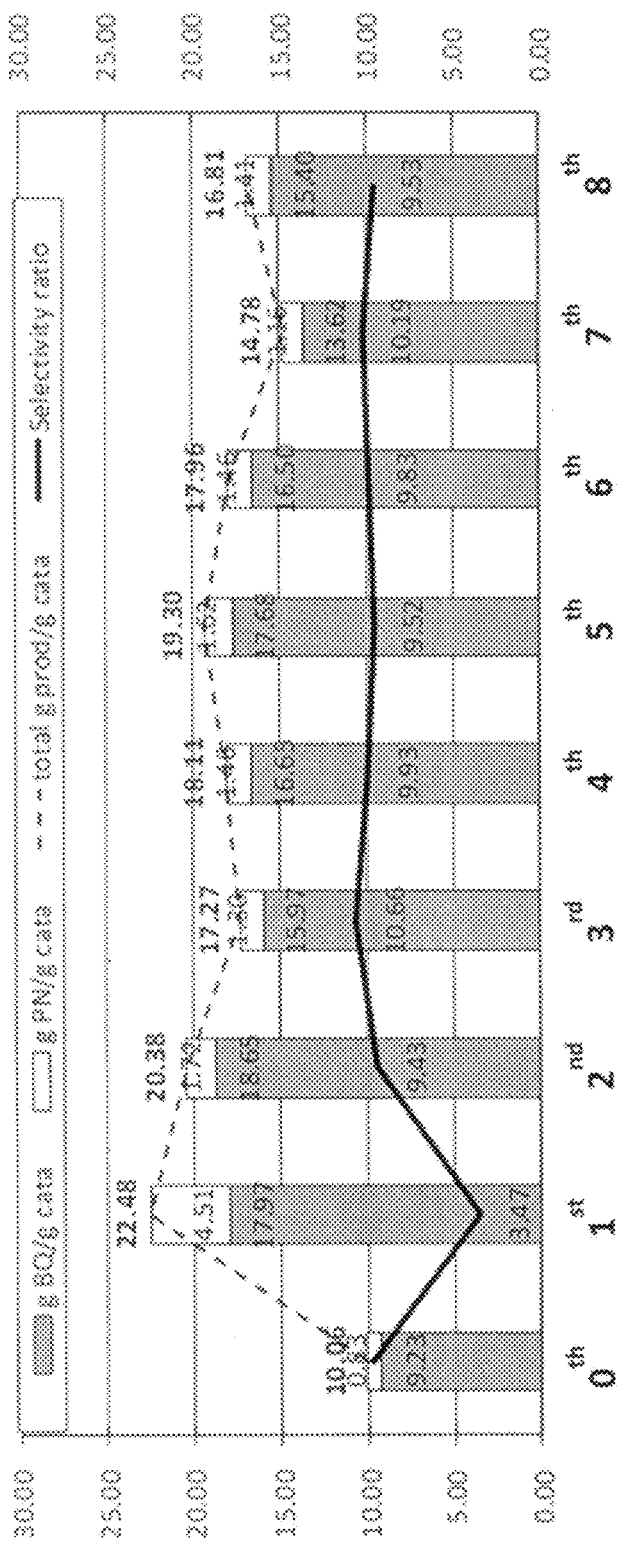
FIG. 4 provides experimental result using elemental copper as a catalyst.

FIG. 4 reports the grams of benzoquinone (BQ) produced per gram of catalyst; grams of phenyl (PN) produced per gram of catalyst; total grams of product produced per gram of catalyst; and the selectivity ratio. Please note that the "selectivity ratio" is the ratio of the desired product formed (in moles) to the undesired product formed (in moles), i.e., moles of hydroquinone produces to the moles of phenol produced. The table below presents the same data provided in FIG. 4 except that the selectivity for the hydroquinone is presented as a percentage of the total products produced (i.e., hydroquinone and phenol). As shown in the table below, in all cases the selectivity for hydroquinone was greater than about 80%; and in all but one case, higher than even 90%.

| Elemental Copper Catalyst (Copper Powder) | | |
| --- | --- | --- |
| Run | Selectivity Ratio (moles of hydroquinone to moles of phenol) | Selectivity Percent (% of hydroquinone compared to total products produced) |
| 0 | 9.72 | 91.7 |
| 1 | 3.47 | 79.9 |
| 2 | 9.43 | 91.5 |

-continued

| | Elemental Copper Catalyst (Copper Powder) | |
|---|---|---|
| Run | Selectivity Ratio (moles of hydroquinone to moles of phenol) | Selectivity Percent (% of hydroquinone compared to total products produced) |
| 3 | 10.66 | 92.5 |
| 4 | 9.93 | 91.9 |
| 5 | 9.52 | 91.6 |
| 6 | 9.83 | 91.9 |
| 7 | 10.19 | 92.2 |
| 8 | 9.53 | 91.6 |

EXAMPLE 3

Synthesis of 2-Methyl-1,4-Benzoquinone with [Cu(MeCN)$_4$]ClO$_4$ Catalyst 2-methyl-1,4-benzoquinone may be prepared by using 4.0 g of [Cu(MeCN)$_4$]ClO$_4$ catalyst dissolved in 350 g of acetonitrile (solvent). 200 g of toluene is added to the mixture. Hydrogen peroxide (10%) is also added (17.2 g of H$_2$O$_2$ and 155 grams of H$_2$O). The reaction temperature is maintained at about 30° C. for 12 hours. The [Cu(MeCN)$_4$]ClO$_4$ catalyst is regenerated after the reaction and the process is repeated multiple times.

EXAMPLE 4

Synthesis of 2,6-Dimethyl-1,4-Benzoquinone with Pure Copper Catalyst 2,6-dimethyl-1,4-benzoquinone may be prepared by using may be prepared by using 3.0 g of pure copper catalyst (copper powder) dissolved in 350 g of propionitrile (solvent). 200 g of m-xylene is added to the mixture. Hydrogen peroxide (10%) is also added (17.2 g of H$_2$O$_2$ and 155 grams of H$_2$O). The reaction temperature is maintained at about 30° C. for 12 hours. The copper catalyst is regenerated after the reaction and the process is repeated multiple times.

EXAMPLE 5

Synthesis of 2-Tert-Butyl-1,4-Benzoquinone with [Cu(MeCN)$_4$]NO$_3$ Catalyst 2-tert-butyl-1,4-benzoquinone may be prepared by using may be prepared by using 3.0 g of [Cu(MeCN)$_4$]NO$_3$ catalyst dissolved in 350 g of acetonitrile (solvent). 200 g of tert-butylbenzene is added to the mixture. Hydrogen peroxide (10%) is also added (17.2 g of H$_2$O$_2$ and 155 grams of H$_2$O). The reaction temperature is maintained at about 30° C. for 12 hours. The [Cu(MeCN)$_4$]NO$_3$ catalyst is regenerated after the reaction and the process is repeated multiple times.

EXAMPLE 6

Synthesis of 2,6-Di-Tert-Butyl-1,4-Benzoquinone with [Cu(MeCN)$_4$]BF$_4$ Catalyst 2,6-di-tert-butyl-1,4-benzoquinone may be prepared by using may be prepared by using 3.0 g of [Cu(MeCN)$_4$]BF$_4$ catalyst dissolved in 350 g of butanenitrile (solvent). 200 g of 1,3-di-tert-butylbenzene is added to the mixture. Hydrogen peroxide (10%) is also added (17.2 g of H$_2$O$_2$ and 155 grams of H$_2$O). The reaction temperature is maintained at about 30° C. for 12 hours. The [Cu(MeCN)$_4$]BF$_4$ catalyst is regenerated after the reaction and the process is repeated multiple times.

EXAMPLE 7

Synthesis of 2-Chloro-1,4-Benzoquinone with Pure Copper Catalyst 2-tert-butyl-1,4-benzoquinone may be prepared by using may be prepared by using 3.0 g of pure copper catalyst (copper powder) dissolved in 350 g of acetonitrile (solvent). 200 g of chlorobenzene is added to the mixture. Hydrogen peroxide (10%) is also added (17.2 g of H$_2$O$_2$ and 155 grams of H$_2$O). The reaction temperature is maintained at about 30° C. for 12 hours. The pure copper catalyst is regenerated after the reaction and the process is repeated multiple times.

The above embodiments are only used to illustrate the principle of the present disclosure and the effect thereof, and should not be construed as to limit the present disclosure. The above embodiments can be modified and altered by those skilled in the art, without departing from the spirit and scope of the present disclosure. Therefore, the protection scope of the present disclosure is defined in the following appended claims. As long as it does not affect the effects and achievable goals of this disclosure, it should be covered under the technical contents disclosed herein.

The terms "comprising," "having," and "including" are used in their open, non-limiting sense. The terms "a" and "the" are understood to encompass the plural as well as the singular. The expression "at least one" means one or more and thus includes individual components as well as mixtures/combinations. The term "about" when referring to a value, is meant specifically that a measurement can be rounded to the value using a standard convention for rounding numbers. For example, "about 1.5" is 1.45 to 1.54. All valued set forth herein can be modified with the term "about" or recited without the term, regardless of whether the term "about" is specifically set forth (or is absent) in conjunction with any particular value. All ranges and values disclosed herein are inclusive and combinable. For examples, any value or point described herein that falls within a range described herein can serve as a minimum or maximum value to derive a sub-range, etc.

The invention claimed is:

1. A process for producing hydroquinone comprising reacting benzene with hydrogen peroxide in the presence of elemental copper catalyst or a copper(I) salt catalyst to form oxidation product comprising benzoquinone and phenol, and converting the oxidation product to hydroquinone by reduction, provided that the selectivity for hydroquinone from benzene is greater than 60%.

2. The process according to claim 1, wherein the catalyst is a copper(I) salt catalyst and the copper (I) salt catalyst is a tetrakis(acetonitrile)copper(I) salt having the following formula:

Cu(CH$_3$CN)$_4$-A, wherein A is an anion.

3. The process of claim 2, wherein the anion is selected from the group consisting of ClO$_4^-$, NO$_3^-$, BF$_4^-$, PF$_6^-$, and CF$_3$SO$_3^-$.

4. The process of claim 1 carried out at a temperature of from 10° C. to 80° C.

5. The process of claim 1, wherein the reaction of benzene with hydrogen peroxide is carried out in a solvent.

6. The process of claim 5, wherein the solvent is selected from the group consisting of nitrile, a $C_3$-$C_7$ ketone, a $C_5$-$C_{10}$ ether, a $C_2$-$C_7$ ester, and a $C_5$-$C_{10}$ hydrocarbon.

7. The process of claim 6, wherein the nitrile is selected from the group consisting of acetonitrile, propionitrile, butanenitrile, and benzonitrile.

8. A process for producing hydroquinone comprising:
   (a) reacting benzene with hydrogen peroxide in the presence of elemental copper catalyst or a copper(I) salt catalyst dissolved in acetonitrile at a temperature of between 10° C. to 80° C.;
   (b) separating a water phase from an oil phase generated in (a);
   (c) adding additional benzene and acetonitrile to the water phase and using azeotropic distillation at a temperature of between 65° C. to 90° C. to remove the water and acetonitrile;
   (d) regenerating the used catalyst in (a);
   (e) separating the mixture of benzoquinone and phenol from the unreacted benzene and acetonitrile;
   (f) recycling the unreacted benzene and acetonitrile of (e) and using it as the additional benzene and acetonitrile added to the water phase in (c); and
   (g) converting the mixture of benzoquinone and phenol to hydroquinone by reduction.

9. The process of claim 8, wherein a selectivity ratio for hydroquinone is greater than about 2.

10. The process according to claim 1, wherein the catalyst is an elemental copper catalyst.

11. The process according to claim 5, wherein the solvent comprises acetonitrile.

12. A process for producing hydroquinone comprising:
   reacting benzene with hydrogen peroxide in solvent in the presence of elemental copper catalyst or a copper(I) salt catalyst to form oxidation product comprising benzoquinone and phenol;
   removing water generated by the reaction of benzene with hydrogen peroxide; and
   converting the oxidation product to hydroquinone by reduction, provided that the selectivity percent for hydroquinone from benzene is greater than 60%.

13. The process according to claim 12, wherein the catalyst is a copper(I) salt catalyst.

14. The process according to claim 12, wherein the copper (I) salt catalyst is a tetrakis(acetonitrile)copper(I) salt having the following formula:

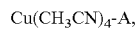

$$Cu(CH_3CN)_4\text{-}A,$$

wherein A is an anion.

15. The process according to claim 12, wherein the catalyst is an elemental copper catalyst.

16. The process according to claim 12 carried out at a temperature of from 10° C. to 80° C.

17. The process according to claim 12, wherein the solvent is a nitrile.

18. The process according to claim 12, wherein the nitrile is acetonitrile.

19. The process according to claim 12, further comprising regenerating the catalyst.

20. The process according to claim 12, further comprising recycling unreacted benzene and solvent.

\* \* \* \* \*